United States Patent [19]

Gedeon

[11] Patent Number: 4,516,573
[45] Date of Patent: May 14, 1985

[54] DEVICE FOR CONNECTING A RESPIRATOR OR ANESTHESIA MACHINE TO A PATIENT

[75] Inventor: Andras Gedeon, Täby, Sweden

[73] Assignee: Gambro Engström AB, Bromma, Sweden

[21] Appl. No.: 466,097

[22] Filed: Feb. 14, 1983

[30] Foreign Application Priority Data

Feb. 23, 1982 [SE] Sweden .................. 8201131

[51] Int. Cl.³ ............................. A61M 16/00
[52] U.S. Cl. ................. 128/201.13; 128/204.18; 128/207.14
[58] Field of Search ............ 128/200.24, 202.26, 128/201.25, 204.18, 205.12, 206.12, 206.11, 205.29, 205.28, 205.27, 206.17, 206.19, 201.13; 55/388, 279, DIG. 33, DIG. 35

[56] References Cited

U.S. PATENT DOCUMENTS

| | | | |
|---|---|---|---|
| 443,191 | 12/1890 | Illing | 55/279 |
| 838,434 | 12/1906 | Morgan | 55/279 |
| 1,596,060 | 8/1926 | Mase | 55/388 |
| 2,702,089 | 2/1955 | Engelder | 55/388 |
| 3,116,969 | 1/1964 | Coleman, Jr. | 55/279 |
| 3,330,284 | 7/1967 | Seman et al. | 55/388 |
| 3,943,940 | 3/1976 | Minami | 131/335 |
| 4,000,341 | 12/1976 | Matson | 128/200.24 |
| 4,090,513 | 5/1978 | Togawa | 128/201.13 |
| 4,200,094 | 4/1980 | Gedeon et al. | 128/201.13 |
| 4,320,756 | 3/1982 | Holmes | 128/200.24 |

FOREIGN PATENT DOCUMENTS

| | | |
|---|---|---|
| 0011847 | 11/1979 | European Pat. Off. |
| 2223474 | 11/1965 | Fed. Rep. of Germany. |
| 1259207 | 1/1968 | Fed. Rep. of Germany ........ 128/201.13 |
| 2230542 | 11/1973 | France. |
| 188504 | 11/1922 | United Kingdom. |
| 416409 | 9/1934 | United Kingdom. |
| 1539217 | 12/1966 | United Kingdom. |
| 1051054 | 12/1966 | United Kingdom. |
| 1458515 | 12/1976 | United Kingdom. |
| 1485458 | 9/1977 | United Kingdom. |
| 649230 | 1/1981 | United Kingdom ........ 128/207.14 |

*Primary Examiner*—Henry J. Recla
*Attorney, Agent, or Firm*—Browdy and Neimark

[57] ABSTRACT

A device for connecting a respirator or an anesthesia machine to a patient comprises a hose (1) which is flexible along substantially its whole length, and one end (1a) of which is formed in a manner to enable it to be connected, in gas-tight fashion, to an endotracheal tube or the like, and the other end (1b) of which is formed in a manner to enable it to be connected, in gas-tight fashion, to the Y-piece of the respirator or anesthesia machine. Incorporated in the part of the hose (1) located nearest the aforementioned other end (1b) is a flexible heat and moisture exchanger body (2) which fills substantially the whole of the cross-sectional through-flow area of the hose (1) and which is substantially uniformly permeable to a gas flow. The heat and moisture exchanger body (2) advantageously comprises a homogenous felted material impregnated with a hygroscopic substance and an anti-bacteria agent. The hose (1) together with the heat and moisture exchanger body (2) incorporated therein form a disposable unit.

7 Claims, 1 Drawing Figure

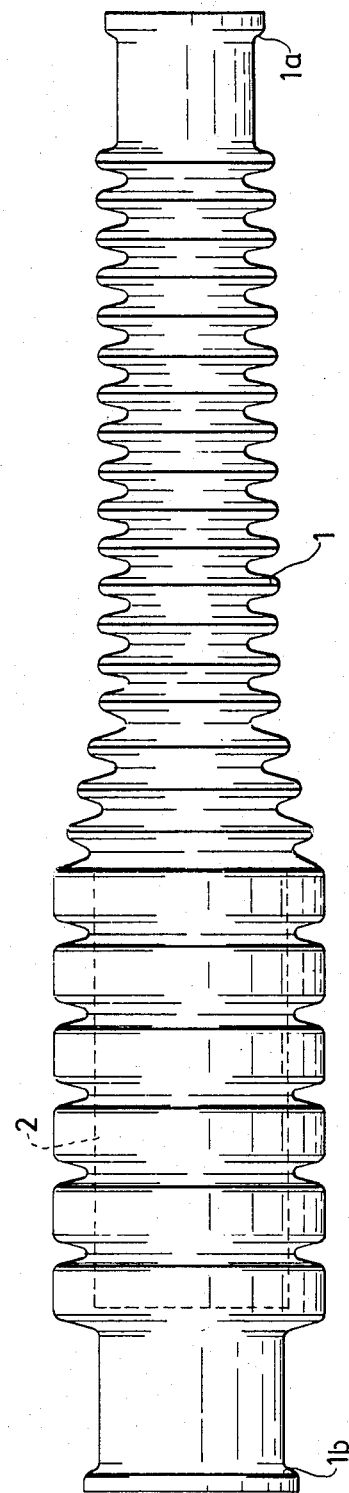

DEVICE FOR CONNECTING A RESPIRATOR OR ANESTHESIA MACHINE TO A PATIENT

The present invention relates to a device for connecting a patient to a respirator or to an anesthesia machine.

In order to connect a patient to a respirator or to an anesthesia machine, a connector is required between the Y-piece coupled to the inspiration and expiration tubes of the apparatus and the patient's trachea, i.e. an endotracheal tube, trachea needle or like device inserted in the trachea of the patient. More often than not, the Y-piece is immoveably arranged, while the patient must be afforded a certain degree of freedom of movement, and hence the aforementioned connector must be flexible. The connector must also be so formed as to ensure that the trachea of the patient is not subjected to additional strain, created by pressure of like forces. It is known to use for such connectors a soft, flexible tube made of a sterilizable rubber material and having a length in the region 15–20 cm and an internal diameter of about 10 mm. To prevent the tube from collapsing when the tube is bent or flexed, it is normal to reinforce the tube wall in some suitable fashion. In itself, such a rubber tube fills all the aforesaid requirements.

Another important requirement when administering respiratory care and anesthetics, is that the gas supplied to the patient is sufficiently humidified. If so is not the case, the walls of the patient's air passage will become dry, with the result that the ability of the trachea to transport mocous is impaired, or ceases completely, which leads to an increased risk of infection and lung complications. One known method of achieving satisfactory humidity of the breathing gas administered to the patient, is to use a heat-moisture exchange system which, as the patient breathes, takes up heat and moisture from expired gas and, during the following inspiration period, delivers heat and moisture to the dry and relatively cool breathing gas administered from the respirator or the anesthesia machine. As will be understood, this heat and moisture exchanger must be connected between the patient and the aforementioned Y-piece. In order to achieve acceptable efficiency, even during long periods of care, the heat and moisture exchanger must have a satisfactory volumetric capacity, and a structure which presents a maximum are of surface contact to the gas flowing therethrough. Heat and moisture exchangers used hitherto for this purpose are formed as separate, rigid units which are coupled between the aforementioned flexible tube and the Y-piece and which have a much larger diameter than the tube, for example a diameter of 25–50 mm, so as to achieve satisfactory heat and moisture exchange efficiency.

The use of these known heat and moisture exchangers, however, is encumbered with a number of disadvantages. For example, the coupling of the flexible tube and the rigid heat and moisture exchanger in series results in an undesirably long and heavy arrangement, which greatly increases the risk of additional strain on the patient's trachea. In addition, there is created an additional joint between the tube and the heat and moisture exchanger, which increases the risk of accidental disconnections. Moreover, it is difficult to achieve a satisfactory transition of the flow of gas between the narrow rubber tube and the heat and moisture exchanger, which is of much larger diameter than the tube. If this transition is poor, the gas flow will be unevenly distributed over the cross-sectional flow area of the heat and moisture exchanger, which means that the heat and moisture exchanger will not be used in the best of ways, and results in increased flow resistance and decreased efficiency. If an attempt is made to solve this problem by changing the design of the heat and moisture exchanger, this will lead to a lengthening of the exchanger, which in itself is a rigid unit, which worsens the aforementioned problems.

Consequently, an object of the present invention is to provide for the purpose of connecting a patient to a respirator or anesthesia machine an improved device which is not encumbered with the aforementioned disadvantages inherent with known such connectors.

In accordance with the invention, this object is achieved with a device which, over substantially the whole of its length, comprises a flexible hose which at one end thereof is formed in a manner to enable it to be connected, in gas-tight fashion, to an endotracheal tube or the like, and which at the other end thereof is formed in a manner to enable it to be connected, in gas-tight fashion, to the Y-piece coupled to the inspiration and expiration tubes of the respirator or anesthesia machine, and in which flexible hose there is incorporated, in the region thereof nearest said other end, a flexible, substantially uniformly gas permeable body of a hygroscopic material which body fills substantially the whole of the cross-sectional flow area of the hose.

By means of the device according to the invention there is obtained, in a highly advantageous manner, between the patient's trachea and the Y-piece of the respirator or anesthesia machine, a connection which is flexible along the whole of its length and which, in addition, is shorter and lighter in weight than the prior art arrangements comprising a separate rigid heat and moisture exchanger connected to a flexible rubber tube. Furthermore, there is one less joint between the patient and the Y-piece.

So that the invention will be more readily understood and further features and advantages afforded thereby made apparent, an exemplary embodiment of a device according to the invention will now be described with reference to the accompanying drawing, the single FIGURE of which is a side view of said device according to the invention.

The device according to the invention illustrated in the drawing comprises a hose 1, which is flexible along substantially the whole of its length and which is formed at one end 1a thereof in a manner which enables it to be connected, in a gas-tight fashion, to an endotracheal tube, a tracheal needle or the like by means of a suitable hose clip or like fastener, while the opposite end 1b of the hose is formed in a corresponding manner, to enable said opposite end to be connected, in a gas-tight fashion, to the Y-piece of a respirator or anesthesia machine by means of a suitable hose clip or like fastener. To enable the hose to be bent or curved readily without risk of collapsing the wall of the hose is advantageously given a bellows or corrugated form, in the illustrated manner.

Incorporated in that part of the hose located nearest the end 1b arranged for connection to the Y-piece, is a heat and moisture exchanger member or body 2. The exchanger 2 is so designed that it substantially completely fills the through-flow area of the hose 1 and has a structure which permits gas to flow therethrough with uniform distribution over the flowarea. The structure is also such as to make the exchanger 2 flexible in itself, so that the part of the hose 1 incorporating the exchanger 2 can also be flexed and curved. For example, the exchanger 2 may conveniently comprise a body or mass of a homogeneously felted material, for example a polypropylene fibre, which is impregnated with a hygroscopic substance, such as magnesium chloride or lithium chloride.

So that the heat and moisture exchanger 2 has a volume sufficient to satisfy the desired exchange of heat and moisture, the part of the hose 1 incorporating the exchanger 2 has a diameter which is larger than the diameter of the remainder of the hose. Transition between the two diameter values takes place gradually, as illustrated in the drawing, so that gas can flow through the device with the least possible resistance, and so that the gas will flow with uniform distribution through the whole of the volume of the heat and moisture exchanger body 2, thereby effectively utilizing said volume for heat and moisture exchange purposes.

The felted material in the heat and moisture exchanger body 2 may also, to advantage, be impregnated with an antibacteria agent, for example the agent retailed on the market under the tradename Irgasan DP 300. In this way, the Y-piece connected to the end 1b of the hose 1 and the tubes or supply lines extending from the respirator or anesthesia machine and connected to said Y-piece will be effectively protected against microorganisms, thereby greatly reducing the need of sterilizing these parts between different patients.

The structure of the heat and moisture exchanger body 2 in the device according to the invention is such as to prevent it from being effectively sterilized. Consequently, the whole of the device according to the invention, i.e. the hose 1 with the heat and moisture exchanger body 2 incorporated therein, is constructed, to advantage, as a disposable unit, i.e. a unit intended for one-time use only. This means that the material from which the hose 1 is made need not be sterilizable, and hence a much less expensive material can be used than in the case of the previously used connecting tubes of silicone rubber intended for sterilization. The hose 1 of the device according to the invention may, to advantage, be made from a plastics material, for example a material of the type EVA, ELVAX 360, ELVAX 460 or LDPE.

I claim:

1. A device for connecting a Y-piece connected to the inspiration and expiration tubes of a respirator or an anesthesia machine to an endotracheal tube or the like adapted to be attached to a patient, comprising a hose which is continuous and flexible along substantially its whole length and which at one end thereof includes means formed in a manner to enable it to be connected, in gas-tight fashion, to said endotracheal tube or the like, and which at the other end thereof includes means formed in a manner to enable it to be connected, in gas-tight fashion, to said Y-piece coupled to the inspiration and expiration tubes of the respirator or anesthesia machine, and inside said flexible hose there is permanently incorporated, in the region thereof adjacent said other end, a heat and moisture exchanger consisting of a flexible, substantially uniformly gas permeable body of a felted fibrous material impregnated with a hygroscopic substance, said body filling substantially the whole of the cross-sectional flow area of the hose.

2. A device as claimed in claim 1, wherein said felted material is further impregnated with an antibacteria substance.

3. A device as claimed in claim 1, wherein said felted material comprises polypropylene fibres.

4. A device as claimed in claim 1, wherein the part of said hose incorporating said heat and moisture exchanger body has a larger diameter than the remainder of the hose, the transition between the two diameter values being gradual.

5. A device as claimed in claim 1, wherein said hose and said heat and moisture exchanger body incorporated therein have the form of a disposable unit.

6. A device as claimed in claim 1, wherein said hose is made of a plastics material.

7. A device as claimed in claim 1, wherein the wall of said hose has the form of a bellows structure.

* * * * *